United States Patent [19]

Tabuchi et al.

[11] 4,270,543

[45] Jun. 2, 1981

[54] SILVER-SILVER CHLORIDE ELECTRODE

[75] Inventors: Katsuhiko Tabuchi; Toshiaki Kato; Kenryo Namba, all of Tokyo, Japan

[73] Assignee: TDK Electronics Co., Ltd., Tokyo, Japan

[21] Appl. No.: 82,660

[22] Filed: Oct. 9, 1979

[30] Foreign Application Priority Data

Oct. 6, 1978 [JP] Japan .............................. 53-122706
Nov. 17, 1978 [JP] Japan .............................. 53-140954

[51] Int. Cl.³ ............................................. A61B 5/04
[52] U.S. Cl. .................................... 128/639; 128/640
[58] Field of Search ............................... 128/639–641, 128/643, 644, 783, 803; 252/514

[56] References Cited

U.S. PATENT DOCUMENTS

| 3,547,835 | 12/1970 | Short | 252/514 |
| 3,649,567 | 3/1972 | Short | 252/514 |
| 3,665,064 | 1/1970 | Mosier et al. | 128/639 |
| 3,747,590 | 7/1973 | Motley | 128/639 |
| 3,755,723 | 8/1973 | Short | 252/514 |
| 3,834,373 | 9/1974 | Sato | 128/641 X |
| 3,846,345 | 11/1974 | Mason et al. | 252/514 |
| 3,944,696 | 3/1976 | Larry | 252/514 X |
| 4,112,941 | 9/1978 | Larimore | 128/641 |

FOREIGN PATENT DOCUMENTS

| 2912161 | 10/1979 | Fed. Rep. of Germany | 128/640 |
| 51-59488 | 5/1976 | Japan | 128/639 |

Primary Examiner—Lee S. Cohen
Attorney, Agent, or Firm—Oblon, Fisher, Spivak, McClelland & Maier

[57] ABSTRACT

A silver-silver chloride skin electrode is prepared by coating a composition containing silver grain, silver chloride grain and glass frit on a substrate made of a spinel type crystalline oxide such as ferrite and sintering the coated layer. The electrode is durable to an electroconductive paste.

6 Claims, 9 Drawing Figures

SILVER-SILVER CHLORIDE ELECTRODE

BACKGROUND OF THE INVENTION

1. Field of the Invention

The present invention relates to a silver-silver chloride electrode. More particularly, it relates to a silver-silver chloride skin electrode adapted to a skin of a living-body for detecting electrical signal generated by biopotential phenomena such as electrocardiogram, electromyogram and electroencephalogram to lead the electrical signal to a monitoring equipment.

2. Description of the Prior Arts

When a biopotential phenomenon is measured by the electrocardiogram, and the electroencephalogram etc., the bipotentials are very weak, for example, on the order of several mV. Thus, in order to detect precisely the biopotentials and to lead it to a monitoring equipment, the skin electrode adapted to a skin of a living-body should have stable electrode potentials, small electrode impedance and should not cause noise potentials. Thus, the skin electrode should impart highly reversible electrode reaction as a nonpolarized electrode.

It has been known that a silver-silver chloride electrode is optimum as the biopotential nonpolarized electrode.

It has been reported that the silver-silver chloride electrode having excellent characteristics as a skin electrode is prepared by electrolyzing a silver plate as an anode in an aqueous solution of sodium chloride to form a film of silver chloride on the surface of the silver plate or by press-molding a mixture of powdery silver and powdery silver chloride. However, these processes have various disadvantages that many steps are required and a cost for equipment is expensive and a cost for raw materials is expensive. Such silver-silver chloride electrode is not suitable as a disposable electrode. Thus, the silver-silver chloride electrode has not been widely used.

In order to overcome these disadvantages on the conventional preparation of the silver-silver chloride electrode, it has been proposed to prepare a silver-silver chloride electrode by coating a layer of a homogeneous mixture of silver grain, silver chloride grain and a synthetic resin such as polyvinyl chloride and epoxy resin on a substrate for the electrode in Japanese Unexamined Patent Publication No. 24195/1972. It has been also proposed to prepare a silver-silver chloride electrode by coating on a conductive substrate, a layer having an organic matrix made of epoxy resin, etc. in which silver chloride grain and silver grain or silver coated grain coating silver on a core such as ceramic, silica or glass grain, are dispersed, in Japanese Unexamined Patent Publication No. 26789/1976. It has been also proposed to prepare a silver-silver chloride electrode by bonding silver grain and silver chloride grain with an epoxy resin adhesive on a metal surface such as silver, in Japanese Unexamined Patent Publication No. 59488/1976.

These silver-silver chloride electrodes are prepared by forming the coated layer on the substrate whereby the disadvantages of the conventional processes are not found and stable electrode potential (off-set voltage) characteristic is given and noise and fluctuation of base line are small. However, medical requirements such as surgical operations with a electric knife in monitoring an electrocardiograph have been increased and large input noise may be applied together with the biopotentials in many cases. The large input noise may cause the voltage on the order of 1 Volt or the current on the order of several mA. When such large input noise is applied, high polarization is caused by the known silver-silver chloride electrode so that it is not practically used to be inoperative.

The inventors have studied to develop a stable silver-silver chloride electrode which is easily prepared and economical and is suitable as disposable skin electrode and has stable off-set voltage characteristic and does not cause substantial noise and fluctuation of the base line and maintains non-polarizability during the input of large input noise caused by an electric knife, etc.

The inventors have found and proposed an improvement of the conventional silver-silver chloride electrode having a coated layer of silver grain, silver chloride grain and an organic matrix on a conductive substrate by substituting the silver grain by carbon grain coated with silver so that the skin electrode is easily prepared and has stable off-set voltage characteristic and has improved non-polarizability under the unpredictable large input noise.

The skin electrode has excellent characteristics as illustrated. However, as the conventional technological problems, the layer of silver grain, silver chloride grain and an organic polymer as the matrix is bonded on the substrate so that there is the disadvantage of relatively weak adhesive strength between the coated layer and the substrate. Even though, the skin electrode is disposable, high adhesive strength between the coated layer and the substrate is required for the silver-silver chloride electrode. In order to satisfy the requirement on the adhesive strength, a ratio of the organic matrix should be high so as to cause inferior electric characteristic of the skin electrode. On the other hand, in order to impart excellent electric characteristics, the ratio of the organic matrix should be decreased so as to cause inferior adhesive strength, higher defect rate in the production or inferior storagable characteristic of the skin electrode. In measurements by using the skin electrode, an electroconductive cream or jelly containing an electrolyte is placed between the skin electrode and the skin so as to decrease the contact-resistance and the fluctuation of the contact resistance. In the case of the disposable skin electrode, the cream or the jelly is immersed in sponge and the sponge is placed on the coated layer of the skin electrode held in a casing. When the disposable skin electrode is stored for a long time, the coated layer is deteriorated by the component of the electroconductive cream or jelly, so as to deteriorate the electric characteristics and the adhesive strength.

SUMMARY OF THE INVENTION

It is an object of the present invention to overcome said disadvantages and to provide a skin electrode which can be easily economically produced by coating an electrode layer on a substrate to be suitable as a disposable skin electrode and has stable off-set voltage characteristics and small noise and small fluctuation of the base line and imparts excellent non-polarizability even though a large input noise is applied to the biopotentials by an electric knife etc.

It is another object of the present invention to provide a skin electrode which has high adhesive strength between an electrode layer and a substrate so as to be high non-defect percent in the production and can be stored for a long period without deterioration of the adhesive strength and the electric characteristics even though it is stored in the condition immersing the electroconductive cream or jelly.

The foregoing and other objects of the present invention have been attained by providing a silver-silver chloride electrode having an electrode layer of silver grain, silver chloride grain and a glass matrix coated on a conductive substrate.

BRIEF DESCRIPTION OF THE DRAWING

FIG. 2 is a graph showing the variation of input current wherein the time is plotted on the abscissa and the current is plotted on the ordinate;

FIGS. 3($a$) to ($g$) are respectively graphs showing each variation of each potential difference between a pair of the electrodes wherein the time is plotted on the abscissa and the potential difference is plotted on the ordinate.

DETAILED DESCRIPTION OF THE PREFERRED EMBODIMENTS

Figure 1:
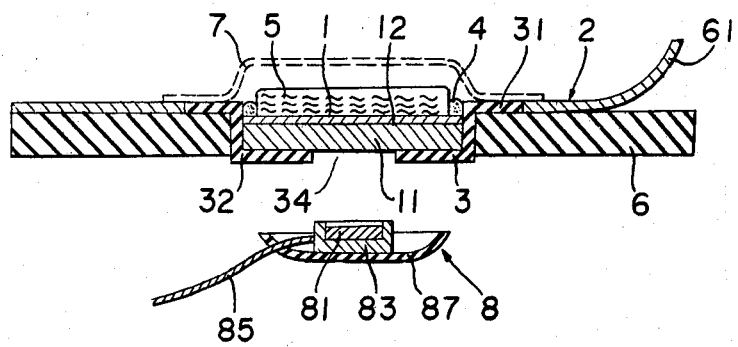
FIG. 1 is a sectional view of skin electrode assembly using a silver-silver chloride electrode of the present invention.

The coated layer of the electrode of the present invention is made of silver grain, silver chloride grain and glass frit having low melting point.

The glass frit having low melting point can be amorphous or crystalloid and should have a melting point of lower than 700° C. preferably lower than 650° C. especially 400° to 650° C.

The glass frit can be boron glass made of $B_2O_3$ and one or more of PbO, ZnO and $SiO_2$ in which one or more of additional components of $Tl_2O$, $Bi_2O_3$, CdO, BaO, $Li_2O$, $Na_2O$, $K_2O$, $V_2O_3$ and $Al_2O_3$ can be incorporated. It is preferable to be $B_2O_3$-PbO-ZnO type, $B_2O_3$-PbO-$SiO_2$ type and $B_2O_3$-ZnO-$SiO_2$ type as the boron glass. The additional component can be incorporated in these type glass. The ratio of the components can be selected as desired so as to give the glass frit having low melting point.

It is preferable to use the glass frit having a grain size of 100 mesh pass. A commercially available electroconductive paste containing the glass frit having low melting point and silver grain such as silver paste 4040A manufactured by Shoei Kagaku K.K. can be used.

The silver grain incorporated in the coated layer can have spherical shape or flaky shape and can be solid silver grain and also can be a silver coated grain prepared by coating silver on core grain made of alumina, silica, TiC, SiC, Cu, Al, glass, graphite or other carbon grain. The selection of the solid silver grain or silver coated grain can be considered in view of amount and cost of silver grain and silver coated grain.

In the case of the organic matrix, the silver coated carbon grain is preferable to impart excellent electric characteristics especially non-polarization characteristics in the application of the large input noise. However, in the case of the glass frit in the present invention, it is preferable to use the solid silver grain.

In both cases, the silver grain having an average particle diameter of 0.05 to 10$\mu$ is preferable to impart desired characteristics.

The silver grain can be produced by the known processes and also can be commercially available silver grain. In the case of the silver coated grain, a ratio of silver to the core is preferably at a ratio of 95 to 60 wt. %. The silver coated grain can be produced by various known processes and also can be commercially available one.

In the specification, the silver grain means the solid silver grains and also the silver coated grains.

Silver chloride grain can be prepared by crystallizing silver chloride from an aqueous solution of a water soluble silver salt and filtering and washing the silver chloride and if necessary, pulverizing or sieving the silver chloride and also can be commercially available one. The silver chloride grain having an average particle diameter of less that 100$\mu$ is preferably used.

The silver grain and the silver chloride grain are preferably incorporated at ratio of the silver chloride grain: silver grain of 0.01 to 2:1 preferably 0.1 to 1:1 by weight.

The glass frit is preferably incorporated at a ratio of 0.01 to 0.2 wt. part to 1 wt. part of the silver grain.

The coated layer is preferably formed to have a thickness of 0.1 to 1 mm.

The conductive substrate on which the coated layer is formed, can be made of any electroconductive substrate which can be a substrate made of a conductive material itself or an insulating substrate on which an electroconductive material is coated to impart the electroconductive property.

The electroconductive material can have specific resistance of less than $10^3$ $\Omega$ cm. Thus, the substrate can be made of various metals, electroconductive ceramics, electroconductive rubbers.

In the production of the electrode of the present invention, the heat-treatment is carried out after coating the paste on the substrate and accordingly, it is preferable to use a metal such as silver, copper and stainless steel or an electroconductive ceramic such as ferrite. In the case of the disposable skin electrode, it is preferable to have a form of an assembly of a base comprising the substrate coated with the layer which is fitted in a casing and a terminal part connecting to an instrument for measurement by a lead wire connected to the base so that the base is disposable.

The electric connection of the base and the terminal part can be a snapped connection between a projection in the base and a groove in the terminal part by a jack system, a clip system and a hook system. In the snapping, certain pressure is applied whereby the electroconductive cream immersed in the sponge or coated between the electrode layer and the skin is squeezed out of the desired measuring place and the effective area is varied and the accuracy is decreased and the tackiness such as a tacky tape for fixing the substrate on the skin is decreased. In order to overcome the disadvantages, it has been proposed to use a magnetic substance as the substrate and a permanent magnet is fixed in the terminal part to attain the electric connection by the contact of them.

The substrate can be made of magnetic metal, however, the magnetic metal is usually lower than hydrogen so as to cause variation of the off-set voltage when the magnetic metal contacts with an aqueous solution of an electrolyte containing in the electroconductive cream. The substrates which have not such trouble include spinel type magnetic oxides, magnetite and ferrite.

The magnetite can be prepared by the known melting method and the known sintering method.

The ferrite can be the spinel type sintered product having more than 50 mole % of iron oxide component as $Fe_2O_3$ and less than 50 mole % of the other oxide component selected from the group consisting of manganese oxide, nickel oxide, cobalt oxide, magnesium oxide, copper oxide, zinc oxide and cadmium oxide. The spinel type sintered product can be prepared by the known process.

The silver-silver chloride electrode of the present invention can be prepared by the following process.

The composition for the coating layer is prepared.

The silver grain, the silver chloride grain and the glass frit are dispersed in a suitable medium at desired ratios for forming the composition.

The medium can be an organic medium or water. Suitable media include ketones such as methyl ethyl ketone, aromatic media such as dibutyl phthalate, diethyl phthalate and xylene; cyclohexanone, butyl carbitol acetate, and diacetone alcohol etc.

The medium is usually incorporated at a ratio of 0.1 to 2 by weight based on the silver grain. It is possible to incorporate a known dispersing agent at a desired ratio.

In the composition for the coating, a resin component such as alkyd resin and cellulose derivative can be incorporated at a ratio of 0.1 to 0.5 by weight based on the silver grain.

It is also possible to prepare the composition for the coating by incorporating silver chloride grain in the commercially available electroconductive paste containing the silver grain and the glass frit in a medium.

The composition for the coating is placed on the substrate by a brush coating or a screen printing and then is usually heat-treated at about 400° to 650° C. to fix the coated layer on the substrate. The heat-treatment can be carried out in air, if necessary, under controlling the oxygen partial pressure.

Referring to FIG. 1, one preferable embodiment of the skin electrode assembly having the resulting silver-silver chloride electrode will be illustrated.

The skin electrode comprises the base (2) and the terminal part (8). The base (2) is usually a disposable form. The base (2) is formed by assembling the silver-silver chloride electrode (1) in the case (3). The silver-silver chloride electrode (1) comprises a silver-silver chloride electrode layer (12) formed on the spinel type oxide substrate (11) and the case (3) is made of an electric insulating material such as plastic and is molded in a cylindrical form. A flange (31) is formed at the top of the cylindrical body and fitting part (32) is formed at the reverse side. An opening (34) is formed on the fitting part (32). The electrode 1 is fitted so as to contact the substrate (11) with the fitting part in the inner wall of the case (3). In the case (3), a sponge (5) is disposed on the electrode layer (12) of the electrode (1). An insulating resin mold (4) is filled between the inner wall of the case (3) and the sponge (5) or the electrode (1) so as to fix the electrode (1) and the sponge (5) in the case (3).

The case (3) is fitted to a fixing ring (6) made of a foamed resin or a sponge in the form of a disc having a hole at the center. The fixing ring (6) is fixed to the flange (31) of the case (3) with an insulating binder.

A tackifier is coated on the surface of the fixed ring (6) (the upper surface in the drawing), and a releasable paper (61) is covered on the tackifier in the storage and it is peeled off and the tackifier surface is bond to the skin so as to fix the base (2) on the skin. Before fixing the base (2) on the skin, the electroconductive jelly or cream should be immersed in the sponge (5). Thus, the jelly or cream is immersed in the sponge (5) before the fixing or the jelly or cream is immersed in the sponge (5) in the preparation of the base (2). In the latter case, a platen resin cover (7) is bonded on the releasable paper (61) as shown in FIG. 1 so as to protect the jelly or cream immersed in the sponge (5) during the storage and the cover (7) and the releasable paper (61) are taken out before the use.

The terminal part (8) comprises a case (83) made of an electroconductive magnetic substance such as iron and has a cylindrical form having an end face. A permanent magnet (81) is fixed in the case (83) and one end of a lead wire (85) is soldered on the outer surface of the case (83). A cover (87) is bonded on the end face of the case (83).

The skin electrode assembly having said structure is used by fixing the body (2) on the skin and the case (83) of the terminal part is approached to the opening (34) of the end face of the case (3) of the body (2). Thus, the permanent magnet (81) is attracted to the substrate (11) of the electrode (1) in the base (2) by the attraction of the permanent magnet. Thus, the cover (83) is brought into contact with the substrate (11) in the opening (34) of the case (3), and the electrode (1) is connected through the lead wire to the instrument for measurement. Accordingly, the external pressure is not applied for the connection of the body and the terminal part and the troubles of the peeling of the base in the connection or the measurement error can be minimized.

The present invention will be further illustrated by certain examples and references which are provided for purposes of illustration only and are not intended to be limiting the present invention.

EXAMPLE 1

A mixture of 90 mole % of $Fe_2O_3$ and 10 mole % of NiO was thoroughly mixed in a ball mill for about 20 hours and was calcined at 800° C. for about 3 hours. The calcined product was cooled and pulverized in a ball mill for about 20 hours to obtain fine powder having an average diameter of less than $20\mu$. The fine powder was molded under the pressure of 1 ton/cm² to obtain 24 pieces of disc molded products having a diameter of 10 mm and a thickness of 1 mm. The molded products were gradually heated from the room temperature to 1400° C. in a nitrogen gas containing less than 5 vol. % of oxygen and sintered for about 3 hours and annealed during longer than 20 hours in the same gas to obtain a spinel type sintered ferrite substrates having 10 mole % of NiO component.

Silver grain; a solid silver grain having an average particle diameter of $1.8\mu$ for an electroconductive paste commerciallized as TCG-1 by Tokuriki Kagaku Kenkyusho K.K. Silver chloride grain; an aqueous solution of silver nitrate was mixed with an aqueous solution of sodium chloride and the reaction mixture was filtrated, washed, dried, pulverized and sieved through a 250 mesh screen to obtain silver chloride grain.

The silver grain and the silver chloride grain were admixed with the following glass frit, the resin and the medium at the following ratios and the mixture was mixed to form a paste by rotating an alumina porcelain pot (flint pebbles alumina) for 20 hours. Thus, the composition A for the coating was obtained.

Silver grain (Average diameter of $18\mu$ solid silver): 70 wt. parts

Silver chloride grain (less than 250 mesh): 25 wt. parts

Glass frit ($10B_2O_3$-$80PbO$-$10SiO_2$ glass frit: $1-10\mu$): 5 wt. parts

Cellulose resin: 15 wt. parts
n-Butylcarbitol acetate: 50 wt. parts

The resulting composition was coated on the ferrite substrates by a brush and the coated product was dried at 100° C. for 10 minutes and baked at 520° C. for 15 minutes to obtain 24 pieces (12 pairs) of the silver-silver chloride electrodes (a thickness of the coated layer of about 300μ) of the present invention.

Twenty four pairs of the bases (2), (2) and the terminal parts (8), (8) were prepared by using 24 pieces of the silver-silver chloride electrodes. In each sponge (5), an electroconductive cream commerciallized by Fukuda Denshi K.K. was immersed.

Five pairs of the bases (2), (2) were used by peeling of each releasable paper (61) and were brought into contact so as to face the electrode layers (12), (12) of the bases (2), (2) through the sponges (5), (5). Each terminal part (8) was connected to each base (2) of the bonded bases (2) and each potential difference between the electrodes (1), (1) continuously was measured by a voltmeter having high input impedance. Thus, the off-set voltage characteristics of the electrode of the present invention was tested. Five pairs of the electrodes 1-1, 1-2, 2-1, 2-2, . . . 5-1, 5-2 were tested. The results are shown in Table 1.

TABLE 1

| Electrode No. | at contact | Potential difference between electrode terminals (mV) | | | | | |
|---|---|---|---|---|---|---|---|
| | | after 1 min. | after 10 min. | after 30 min. | after 1 hr. | after 10 hr. | after 24 hr. |
| At preparation | | | | | | | |
| 1-1/1-2 | 0.34 | 0.33 | 0.26 | 0.23 | 0.16 | 0.12 | 0.10 |
| 2-1/2-2 | 0.42 | 0.43 | 0.33 | 0.27 | 0.21 | 0.17 | 0.14 |
| 3-1/3-2 | 0.38 | 0.38 | 0.31 | 0.26 | 0.24 | 0.19 | 0.17 |
| 4-1/4-2 | 0.22 | 0.24 | 0.21 | 0.20 | 0.14 | 0.13 | 0.09 |
| 5-1/5-2 | 0.35 | 0.35 | 0.29 | 0.24 | 0.20 | 0.15 | 0.11 |
| After 6 months | | | | | | | |
| 7-1/7-2 | 0.25 | 0.25 | 0.24 | 0.20 | 0.17 | 0.12 | 0.08 |
| 8-1/8-2 | 0.13 | 0.13 | 0.12 | 0.10 | 0.08 | 0.07 | 0.07 |
| 9-1/9-2 | 0.16 | 0.15 | 0.13 | 0.13 | 0.10 | 0.08 | 0.06 |
| 10-1/10-2 | 0.22 | 0.21 | 0.17 | 0.16 | 0.11 | 0.07 | 0.08 |
| 11-1/11-2 | 0.15 | 0.15 | 0.12 | 0.13 | 0.10 | 0.08 | 0.05 |

From Table 1, it is clearly understood that the silver-silver chloride electrode of the present invention had remarkably small noise and stable off-set voltage characteristics.

In order to evaluate stability to a large input noise having a current of about several mA, variations of polarization characteristics by the large input noise were tested.

In these tests, a pair of the bases (2) were brought into contact and each terminal part (8) was connected to each base (2).

Figure 2:
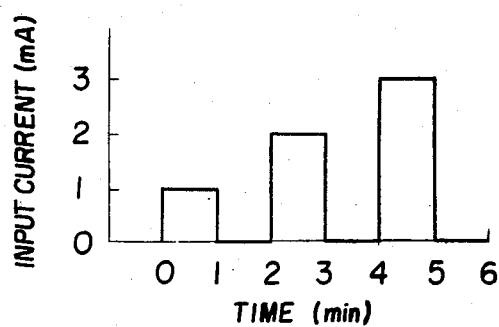
FIGS. 2 and 3 are respectively diagrams showing polarization characteristics of the electrode of the present invention in the application of a large input noise.

As shown in FIG. 2, a DC current was passed for 1 minute and interrupted for 1 minute and the input was varied sequentially in steps of 1 mA, 2 mA, 3 mA . . . and potential differences between the electrodes (1), (1) were continuously measured.

Figure 3:
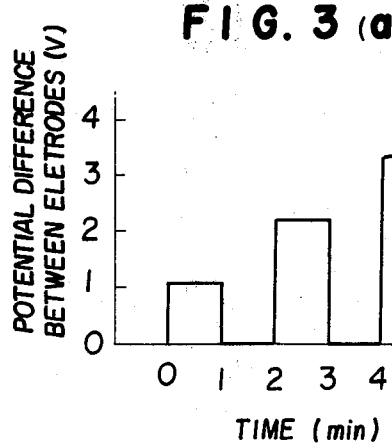
Figure 3:
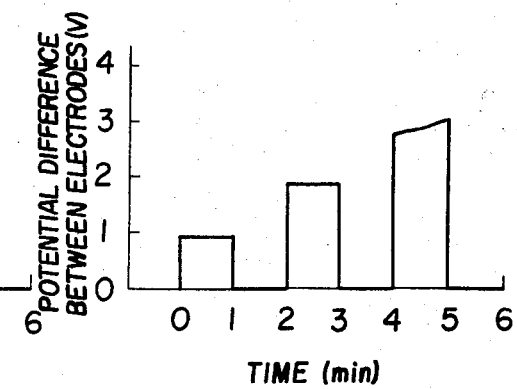

The result by using the pair of the electrodes (6-1), (6-2) is shown in FIG. 3(a). As it is clearly understood from FIG. 3(a), the plat voltage response characteristic is given during the current feeding and excellent ohmic characteristic and non-polarizability in the application of large input noise by the electrodes of the present invention.

After the interruption of the current, the potential difference between the electrodes was recovered to the desired level for the measurement of the electrocardiograph. The non-polarizability during the current feeding is confirmed.

With regard to the electrodes 7-1, 7-2 . . . 11-1, 11-2, 12-1, 12-2, the electrodes were stored for 6 months under contacting the electrode with the electroconductive cream after preparing the body (2). Six months after the preparation, five pairs of the electrodes 7-1, 7-2 . . . 11-1, 11-2 were formed and off-set voltage characteristics of the electrodes were tested. The results are shown in Table 1.

Six months after the preparation, one pair of the electrodes (12-1), (12-2) were formed and the polarizability of the electrodes to a large input noise was tested. The result is shown in FIG. 3(b).

Six months after the preparation and the contact with the electroconductive cream, a scratch test on the surface of the electrode was carried out. No deterioration of the adhesive strength was found.

From these results, it was found that the off-set voltage characteristic, the non-polarizability under a large input noise and the adhesive strength of the electrode were not deteriorated by contacting the electroconductive cream with the electrode.

EXAMPLE 2

In accordance with the process of Example 1 except varying the ratios of the silver grain, the silver chloride grain and the glass frit as shown in Table 2, compositions (B) to (D) were prepared.

TABLE 2

| Composition | Silver grain | (weight part) | |
|---|---|---|---|
| | | Glass frit | Silver chloride |
| B | 50 | 5 | 45 |
| C | 70 | 10 | 20 |
| D | 85 | 5 | 10 |

In accordance with the process of Example 1 except using each of the compositions B, C and D, electrodes B, C and D were prepared and the pairs of the electrodes were formed at the preparation and the off-set voltage characteristics and the non-polarizabilities to the large input noise were tested.

Figure 3C:
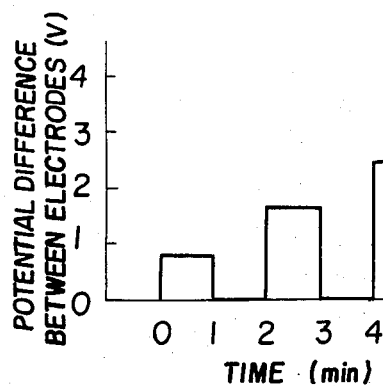
Figure 3D:
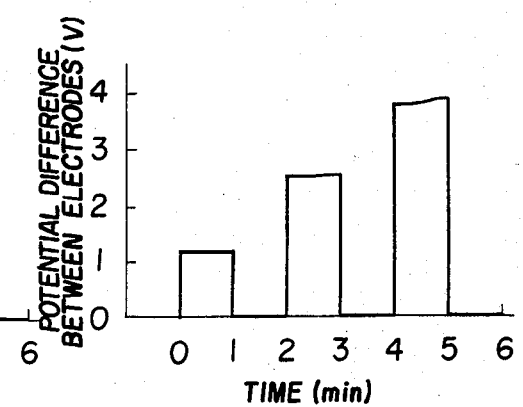
Figure 3E:
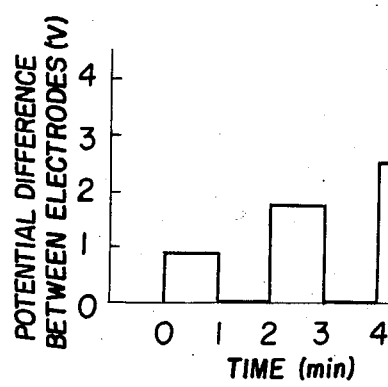

The variation of the off-set voltage characteristics of five pairs of the electrode for each type were continuously measured, the averages of the data are shown in Table 3. The results of the non-polarizabilities of the electrodes B, C and D are respectively shown in FIGS. 3(c), (d) and (e).

TABLE 3

| Time | Potential difference between electrodes (mA) | | |
|---|---|---|---|
| | Electrode pair B | Electrode pair C | Electrode pair D |
| At contact | 0.38 | 0.47 | 0.34 |
| After 1 min. | 0.37 | 0.47 | 0.33 |
| After 10 min. | 0.28 | 0.35 | 0.26 |
| After 30 min. | 0.21 | 0.25 | 0.21 |
| After 1 hour | 0.16 | 0.21 | 0.16 |
| After 10 hour | 0.13 | 0.17 | 0.11 |
| After 24 hour | 0.11 | 0.13 | 0.09 |

From the results, it was found that excellent off-set voltage characteristics and the non-polarizabilities to the large input noise were given as those of Example 1 even though the ratios of the silver grain, the silver chloride grain and the glass frit are changed.

In accordance with the test of Example 1, the resulting electrodes were brought into contact with the electroconductive cream for six months, and the off-set voltage characteristics and the non-polarizabilities to the large input noise were tested. No deterioration was found.

EXAMPLE 3

In accordance with the process of Example 1, a composition E for coating layer was prepared by using the following components.

Silver grain(particle diameter 0.1–1μ): 70 wt. parts
Glass frit ($10B_2O_3$-80PbO-10ZnO glass frit particle diameter 1–10μ): 5 wt. parts
Silver chloride grain(particle diameter less than 100μ): 25 wt. parts
Alkyd resin: 10 wt. parts
Cellulose resin: 10 wt. parts
Cyclohexanone: 40 wt. parts
Methyl ethyl ketone: 20 wt. parts In accordance with the process of Example 1, the composition E was coated on the substrate of Example 1 and treated to form the coated layer having the same thickness and the electrodes were prepared.

In accordance with the test of Example 1, the off-set voltage characteristics and the non-polarizabilities to the large input noise of the electrodes were tested.

The off-set voltage characteristics of five pairs of the electrodes 13-1, 13-2, . . . 17-1, 17-2 are shown in Table 4.

From Table 4, it is clearly understood that the electrodes had excellent off-set voltage characteristics. On the other hand, in accordance with the test of Example 1, the non-polarizabilities to the large input noise were tested. The results were substantially the same as those of FIG. 3(a). The potential differences between the electrodes under the current feeding of 1 mA, 2 mA and 3 mA were reslectively 0.9 V, 1.9 V and 2.8 V to be flat. After the interruption of the current, the potential difference under several mA was immediately recovered to confirm the excellent non-polarizability.

In accordance with the test of Example 1, the electrodes were brought into contact with the electroconductive cream and stored for 6 months, and the electric characteristics and the adhesive strength were tested.

The off-set voltage characteristics and the non-polarizabilities of the electrodes to the large input noise were substantially the same as those of the initial characteristics and the adhesive strength was not deteriorated.

TABLE 4

| Electrode No. | at contact | Potential difference between electrode terminals (mV) | | | | | |
| --- | --- | --- | --- | --- | --- | --- | --- |
| | | after 1 min. | after 10 min. | after 30 min. | after 1 hr. | after 10 hr. | after 24 hr. |
| 13-1/13-2 | 0.47 | 0.45 | 0.37 | 0.28 | 0.23 | 0.16 | 0.13 |
| 14-1/14-2 | 0.55 | 0.54 | 0.38 | 0.27 | 0.20 | 0.18 | 0.14 |
| 15-1/15-2 | 0.16 | 0.22 | 0.23 | 0.15 | 0.13 | 0.07 | 0.08 |
| 16-1/16-2 | 0.33 | 0.35 | 0.21 | 0.17 | 0.15 | 0.12 | 0.09 |
| 17-1/17-2 | 0.42 | 0.41 | 0.35 | 0.22 | 0.20 | 0.14 | 0.11 |

EXAMPLE 4

In accordance with the process of Example 1, a composition F for coating layer was prepared by using the following components.

Silver grain(particle diameter 0.1–1μ): 70 wt. parts
Silver chloride grain (particle diameter less than 100μ): 25 wt. parts
Glass frit ($20B_2O_3$-65ZnO-$15SiO_2$ glass frit particle diameter less than 10μ): 5 wt. parts
Alkyd resin: 10 wt. parts
Cyclohexanone: 40 wt. parts
Dibutyl phthalate: 1 wt. parts In accordance with the process of Example 1, the component F was coated on a ferrite substrate of Example 1 in which 10 mole % of MnO component was incorporated, and treated to form the coated layer having the same thickness and the electrodes were prepared.

In accordance with the test of Example 1, the off-set voltage characteristics and the non-polarizabilities to the large input noise of the electrodes were tested.

The off-set voltage characteristics of five pairs of the electrodes 19-1, 19-2 . . . 23-1, 23-2 are shown in Table 5.

TABLE 5

| Electrode No. | at contact | Potential difference between electrode terminals (mV) | | | | | |
| --- | --- | --- | --- | --- | --- | --- | --- |
| | | after 1 min. | after 10 min. | after 30 min. | after 1 hr. | after 10 hr. | after 24 hr. |
| 19-1/19-2 | 0.29 | 0.31 | 0.25 | 0.18 | 0.12 | 0.08 | 0.09 |
| 20-1/20-2 | 0.13 | 0.16 | 0.24 | 0.23 | 0.15 | 0.10 | 0.06 |
| 21-1/21-2 | 0.41 | 0.40 | 0.36 | 0.27 | 0.22 | 0.14 | 0.11 |
| 22-1/22-2 | 0.42 | 0.44 | 0.38 | 0.31 | 0.24 | 0.15 | 0.10 |
| 23-1/23-2 | 0.36 | 0.35 | 0.27 | 0.21 | 0.16 | 0.13 | 0.09 |

From Table 5, it is clearly understood that the electrodes had excellent off-set voltage characteristics. On the other hand, in accordance with the test of Example 1, the non-polarizabilities to the large input noise were tested. The results were substantially the same as those of FIG. 3(a). The potential differences between the electrodes under the current feeding of 1 mA, 2 mA and 3 mA were respectively flat. After the interruption of the current, the potential difference under several mV was immediately recovered to confirm the excellent non-polarizability.

In accordance with the test of Example 1, the electrodes were brought into contact with the electroconductive cream and stored for 6 months, and the electric characteristics and the adhesive strength were tested.

The off-set voltage characteristics and the non-polarizabilities of the electrodes to the large input noise were substantially the same as those of the initial characteristics and the adhesive strength was not deteriorated.

REFERENCE 1

In accordance with the process of Example 1 except using an organic resin instead of the glass frit in the composition for coating layer, the coated layer was formed on the substrate of Example 1 to obtain a silver-silver chloride electrode as Reference.

A silver coated carbon grain which is commercially available as RDP-90 by Tokuriki Kagaku Kenkyusho K.K., a commercially available silver chloride grain (special grade), ethylenevinylacetate copolymer hot melt resin which is commercially available as AnKa-E-1200 by AnKa Chemical K.K. were mixed at ratios of 10:5:2.5 by weight. Xylene was added at a ratio of 4 wt. parts to 10 wt. parts of the mixture and stirred at 60° C. for 1 hour to prepare a paste as the composition for coating layer.

The paste was coated on the sintered substrate by a brush and heated at 130° C. for 30 minutes and cooled to the room temperature so as to melt-bond it. The silver-silver chloride electrode having a thickness of the coated layer of 200–300μ was obtained.

The electrode for the reference was used to prepare the base (2) and the terminal part (8) shown in FIG. 1. In accordance with the process of Example 1, the releasable paper 61 was peeled off and the pair of the bases (2), (2) were brought into contact so as to face the electrode layers (12), (12) of the bases (2), (2) and the terminal parts (8), (8) were respectively connected to the pair of the contacted bases (2), (2) and the potential difference between the electrodes (1), (1) was continuously measured to study the off-set voltage characteristics. The test was carried out for five pairs of the electrodes. The results are shown in Table 6. (left column)

As shown in Table 6, the electrodes for the reference had remarkably low noises and stable off-set voltage characteristics.

Figure 3F:
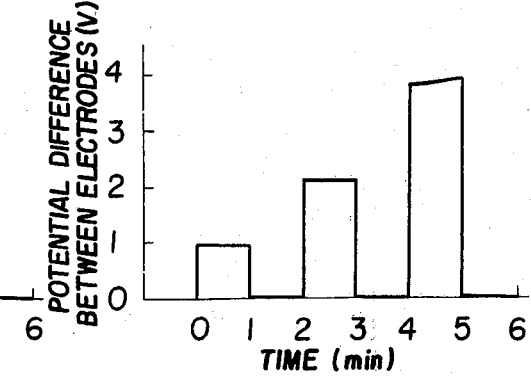

In accordance with the test of Example 1, the non-polarizabilities to the large input noise were measured. The results are shown in FIG. 3(f). The initial off-set voltage characteristic and the initial non-polarizability to the large input noise of the electrodes were substantially the same as those of the present invention.

However, the electrodes were stored in the condition contacting the electrode layers with the electroconductive cream immersed in the sponge (5) in the room.

Figure 3G:
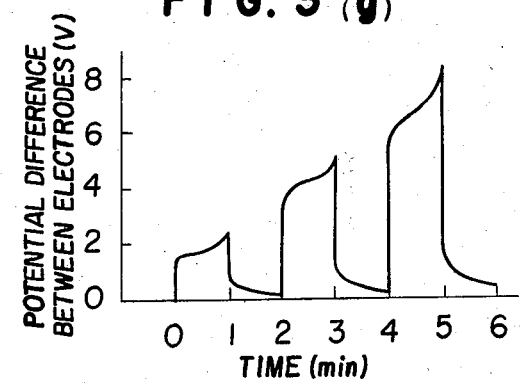

After one week, the non-polarizabilities to the large input noise were tested by the same manner. The results are shown in FIG. 3(g). The polarizability to the large input noise was increased. The stability of off-set voltage characteristics was also inferior as shown in Table 6 right column.

In accordance with the scratch test of Example 1, the coated layer of the electrode was easily peeled off.

TABLE 6

| Time | Potential difference between electrode terminals (mV) | |
| --- | --- | --- |
| at contact | 1.52 | 3.74 |
| after 1 min. | 1.49 | 3.62 |
| after 10 min. | 1.08 | 3.78 |
| after 30 min. | 0.60 | 2.55 |
| after 1 hr. | 0.31 | 2.67 |
| after 10 hr. | 0.25 | 2.94 |

TABLE 6-continued

| Time | Potential difference between electrode terminals (mV) | |
| --- | --- | --- |
| after 24 hr. | 0.14 | 3.03 |

REFERENCE 2

The silver grain and the silver chloride grain of Example 1, and epoxy resin which is commercially available as Daiapond 2000M by Nogami Chemical K.K. were uniformly mixed at ratios of 10:5:0.6 by weight. The mixture was used as the main components of the composition for coating layer. Polyamide resin which is commercially available by Nogawa Chemical K.K. as the epoxy resin hardner was admixed to the mixture at a ratio of 1:1 by weight to the epoxy resin to obtain a paste.

The paste was coated on the substrate of Example 1 by a brush and heated at 100° C. for 1 hour to harden the resin layer. The silver-silver chloride electrode for the reference was obtained.

The initial off-set voltage characteristics and the initial non-polarizability to the large input noise of the electrodes were substantially the same as those of the present invention.

However, the electrodes were stored in the condition contacting the electrode layers with the electroconductive cream.

After one week, the stability of the off-set voltage characteristic was remarkably deteriorated and the polarizability to the large input noise was increased and the coated layer of the electrode was easily peeled off by the scratch test.

We claim:

1. A non-polarizable skin electrode for detecting electrical signals generated by biopotential phenomena, which comprises an electrode layer comprising silver grains, silver chloride grains and particles of glass frit bonded on their surfaces to form a matrix, the grains being interspersed throughout the matrix, the electrode layer being coated upon a substrate.

2. An electrode according to claim 1 wherein said substrate has electroconductivity.

3. An electrode according to claim 2 wherein said substrate is made of a magnetic substance.

4. An electrode according to claim 1 wherein said substrate is an insulator and an electroconductive material is coated on said substrate.

5. An electrode according to claim 4 wherein said substrate is made of a magnetic substance.

6. An electrode according to claim 5 wherein said substrate is made of a spinel type crystalline oxide comprising 100 to 50 mole % of an iron oxide component as $Fe_2O_3$ and 0 to 50 mole % of another oxide component selected from the group consisting of manganese oxide, nickel oxide, cobalt oxide, magnesium oxide, copper oxide, zinc oxide and cadmium oxide.

* * * * *